United States Patent [19]
O'Brien

[11] Patent Number: 5,080,588
[45] Date of Patent: Jan. 14, 1992

[54] SURFACE FINISHING APPARATUS AND METHOD

[75] Inventor: William J. O'Brien, Ann Arbor, Mich.

[73] Assignee: The University of Michigan, Ann Arbor, Mich.

[21] Appl. No.: 631,749

[22] Filed: Dec. 20, 1990

Related U.S. Application Data

[63] Continuation of Ser. No. 212,199, Jun. 27, 1988, abandoned.

[51] Int. Cl.[5] ............................ A61C 3/02; A61O 5/10
[52] U.S. Cl. ..................................... 433/165; 433/24; 433/166; 433/223
[58] Field of Search ............... 433/165, 166, 142, 143, 433/144, 24, 223; 51/206 P; 407/31, 57

[56] References Cited

U.S. PATENT DOCUMENTS

| | | | |
|---|---|---|---|
| 294,192 | 2/1884 | Broadbent | 407/31 |
| 336,777 | 2/1886 | Williams | 433/105 |
| 1,289,325 | 12/1918 | Wake | 433/142 X |
| 1,398,039 | 11/1921 | Olson | 407/31 X |
| 1,461,376 | 7/1923 | Bartlett | 407/57 X |
| 1,868,229 | 6/1932 | Birgbauer | 51/206 P X |
| 2,896,309 | 7/1959 | Jensen | 29/79 |
| 3,894,339 | 7/1975 | Manzi | 433/166 |
| 4,109,385 | 8/1978 | Zahn et al. | 32/59 |
| 4,264,307 | 4/1981 | Neuwirth | 433/166 |
| 4,270,902 | 6/1981 | Wiland | 433/144 |
| 4,353,696 | 10/1982 | Bridges | 433/125 |
| 4,358,893 | 11/1982 | Stanfield | 30/280 |
| 4,473,354 | 9/1984 | Rigand | 433/218 |
| 4,511,334 | 4/1985 | Grafelmann | 433/165 |
| 4,561,214 | 12/1985 | Inoue | 51/165 |
| 4,604,057 | 8/1986 | Viglietti | 433/9 |
| 4,661,059 | 4/1987 | Kanno | 433/9 |
| 4,992,049 | 2/1991 | Weissman | 433/215 |

FOREIGN PATENT DOCUMENTS

| | | | |
|---|---|---|---|
| 389310 | 11/1922 | Fed. Rep. of Germany | 433/165 |
| 936816 | 12/1955 | Fed. Rep. of Germany | 433/166 |

OTHER PUBLICATIONS

Suter Dental Manufacturing Co. Catalog, Jan. 1, 1981, see p., 13, Fig. 15.
Maillefer Dental Co. Catalog 1977 2nd ed. see p. 37, Fig. 193.

Primary Examiner—Robert P. Swiatek
Assistant Examiner—Nicholas D. Lucchesi
Attorney, Agent, or Firm—Rohm & Monsanto

[57] ABSTRACT

Apparatus and method for finishing a surface, such as the surface of a tooth, for improving the strength of an adhesive bond. A plurality of cuts are made into the surface at an angle which is less than 90°. Undercuts are thus formed which enhance the micromechanical engagement between the surface and the solidified adhesive material. The undercuts are dimensioned in response to the viscosity characteristic of the fluid adhesive material so as to promote flow of the fluid adhesive material into the undercuts by capillary action. The undercuts are formed by application of a rotary tool to the surface, the tool having a plurality of spaced-apart edges thereon, which are applied to the surface so that each such cutting edge makes a respective undercut.

4 Claims, 4 Drawing Sheets

SURFACE FINISHING APPARATUS AND METHOD

This application is a continuation of application Ser. No. 212,199, filed June 27, 1988, now abandoned.

BACKGROUND OF THE INVENTION

This invention relates generally to systems for finishing surfaces prior to bonding, and more particularly, to an apparatus and method of preparing a surface for improving micromechanical attachment of applied adhesives.

There is a need for improving the strength of the attachment of adhesives, particularly fluid adhesive materials, to surfaces. The need is particularly acute in the field of dentistry where the wet and enzymatic environment, coupled with the application of extremely high pressures during mastication, have resulted in unacceptably high adhesion failure rates.

One prior art technique for improving the strength of the bond employs abrasion of the surface. Such abrasion generally increases the area of the surface over which the adhesive is applied, resulting in an increase in the bonding strength. Abrasion is effected with the use of sand, abrasion paper, files, and/or rotary tools, depending upon the particular environment where the bond is desired. It is a problem with this approach that the increase in the strength of the bond is primarily a function of the increase in the effective surface area, and this effect does not raise the reliability of the bond sufficiently for some purposes.

It is, therefore, an object of this invention to provide a simple and inexpensive system for improving micromechanical attachment of an adhesive to a surface.

It is another object of this invention to provide a method of finishing a surface of a tooth of a being for improving bonding using dental adhesives.

It is also an object of this invention to provide an apparatus for finishing a surface of a material whereby undercutting is effected.

It is a further object of this invention to provide an apparatus which is used in combination with a rotary tool for finishing a surface of a material whereby undercutting at a predetermined angle is effected.

It is additionally an object of this invention to provide an apparatus which is operated manually for finishing a surface of a material whereby undercutting is effected.

It is yet a further object of this invention to provide a system which ensures total occupation of a plurality of undercuts by a fluid adhesive material.

It is also another object of this invention to provide system for improving bonding strength beyond that which is achieved by conventional roughening of the surface.

It is yet an additional object of this invention to provide a system for improving the strength of a bond between metal parts.

It is still another object of this invention to provide a system for improving the strength of a bond between wood parts.

It is a yet further object of this invention to provide a system for improving the strength of a bond between restorative materials and tooth structure.

It is also a further object of this invention to provide a system for improving the strength of a bond between restorative materials and bone.

SUMMARY OF THE INVENTION

The foregoing and other objects are achieved by this invention which provides, in a first apparatus aspect thereof, a surface finishing instrument for installation on a rotating tool. In accordance with the invention, the surface finishing instrument is provided with a shaft having a coupling end for engaging with the rotating tool and rotating axially in response thereto. The shaft of the surface finishing instrument is also provided with a working end distal from the coupling end. A plurality of thin, substantially circular blades, each having a different diameter, is mounted concentrically on the working end of the shaft, the blades being arranged in a predetermined order responsive to their respective diameters. A plurality of spacers is installed on the shaft, each spacer being disposed between adjacent ones of blades for maintaining a predetermined distance therebetween.

In certain embodiments of the invention, the sequential arrangement of the blades can be selected in response to their respective diameters to produce overall outside contours for the instrument corresponding to a curvature of a surface desired to be subjected to a finishing operation. In a highly advantageous embodiment of the invention, the predetermined order of the blades corresponds to a diametrically increasing order toward the coupling end of the shaft. In this manner, the blades on the shaft form a substantially conical outline with an outline edge at a predetermined angle $\Theta$ with respect to a longitudinal axis of the shaft. Of course, other outline shapes, such as concave, convex, or combination shapes, are included within the scope of the invention.

In a further embodiment of the invention, each of the blades has a thickness which is less than 0.6 mm, and preferably less than 0.5 mm. The thickness of the blades may be selected in response to a viscosity characteristic of a fluid adhesive material. Persons of skill in the art will be able to select a blade thickness which results in a width of surface cut which is optimized for facilitating capillary flow of the fluid into the undercuts on the finished surface. Such dimensioning of the undercuts with respect to the viscosity of the fluid adhesive material will ensure complete penetration into the undercuts and improve the strength of the bond.

In accordance with a further apparatus aspect of the invention, a hand tool is provided for finishing a surface to increase micromechanical bonding strength. The hand tool is provided with a handle portion for facilitating manipulation thereof by a user. A blade portion which is coupled to the handle portion has an edge portion for communicating with the surface during finishing. The edge portion has a plurality of cutting teeth thereon for forming respective cuts into the surface, the cutting teeth being arranged to undercut into the surface at a predetermined angle which is less than 90°.

In an advantageous embodiment of the invention, the cutting teeth are each dimensioned to produce a respective undercut having a width which is less than 0.6 mm, and preferably approximately 0.5 mm. Particularly when used in dentistry for effecting micromechanical bonding, this dimensional limit for an undercut is within a range which facilitates capillary flow of the fluid adhesive material into the valleys of the undercuts. However, in situations where the viscosity characteristic of the fluid adhesive material can be predetermined, such as when working with a known adhesive, the dimensions of the cutting teeth can be selected to form a cut having a width which is determined in response to the viscosity characteristic so as to facilitate capillary flow of the particular adhesive fluid into the cuts in the finished surface.

The hand tool of the present invention, in a practical embodiment thereof, has the cutting teeth configured to have a substantially straight cutting edge on one side thereof, and a curved cutting edge on another side thereof. The substantially straight and curved cutting edges meet one another discontinuously, illustratively at a point. When used in the field of dentistry to provide a finish to the surface of a tooth to enhance bonding strength, or micromechanical attachment, the direction of the undercut, on the side of the tooth, is inwardly and away from the gum. The curved cutting edges are directed toward the gum, and the tool is drawn along the tooth, in a direction substantially parallel to the gum, whereby each cutting tooth forms its respective undercut.

In accordance with a method aspect of the invention, a surface is finished in a manner which enhances engagement of the surface with a fluid adhesive material. The method includes the steps of forming a plurality of substantially parallel cuts into the surface at a predetermined angle with respect thereto less than 90° to form undercuts therein and applying the fluid adhesive material onto the finished surface. The fluid adhesive material has a viscosity characteristic which facilitates capillary flow into the undercuts, the width of the undercuts being selectable by persons of skill in the art to ensure such capillary flow.

In embodiments of the invention where the surface to be treated, or finished, is the surface of a tooth, the fluid adhesive material can be one of several commercially available dental adhesives. The dental adhesives may be, for example, those which are marketed under the trade names ADHESIT, PRISMA BOND, or SCOTCHBOND.

In accordance with a further method aspect of the invention, the step of forming includes the further steps of rotating a plurality of blades arranged in predetermined space relation, and applying the plurality of blades simultaneously to the surface at a predetermined angle with respect thereto which is less than 90°.

In accordance with a still further method aspect of the invention, the step of forming includes the further steps of engaging with the surface to be finished a blade having a plurality of substantially aligned cutting teeth arranged at a predetermined angle with respect to the surface which is less than 90°, and drawing the blade along the surface in a direction transverse to the alignment of the cutting teeth.

BRIEF DESCRIPTION OF THE DRAWING

Comprehension of the invention is facilitated by reading the following detailed description, in conjunction with the annexed drawing, in which.

DETAILED DESCRIPTION

Figure 1:
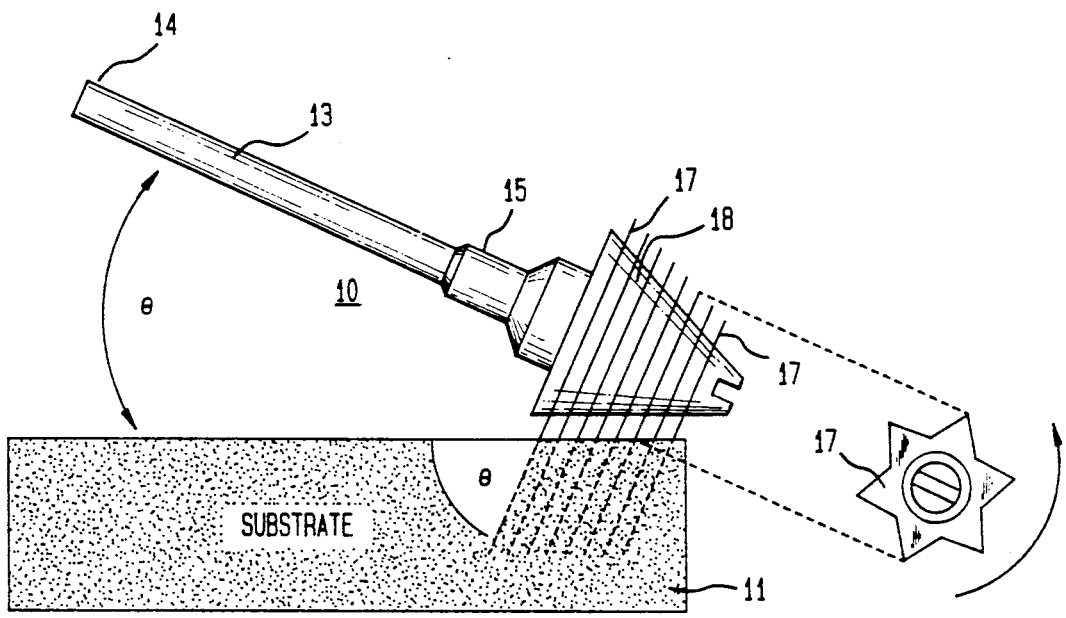
FIG. 1 is a schematic plan view of a rotary tool which produces undercuts in a substrate material prior to bonding, in accordance with the invention.

FIG. 1 is a schematic plan view of a rotary tool 10 constructed in accordance with the invention for producing undercuts in a substrate material 11, prior to the application of a fluid adhesive material (not shown in this figure). As shown rotary tool 10 has a shaft 13 with a shaft coupling end 14 and a shaft working end 15. The shaft coupling end is adapted for coupling in a known manner to a rotation device (not shown), such as a dental drill.

In the specific illustrative embodiment, shaft working end 15 is provided with a plurality of rotary blades 17 having different effective diameters. The blades are arranged coaxially on shaft 13, and in an order determined by their effective diameters. In this specific arrangement, the diameters of rotary blades 17 increase toward shaft coupling end 14 so as to form a substantially conical outline. A plurality of spacers 18 are arranged intermediate of rotary blades 17, the spacers having different diameters also.

Each of rotary blades 17 has a configuration adapted for cutting along its edge, as shown in the plan projection of this figure. In this specific illustrative embodiment, the rotary blades have star-like shapes, but any other shape can be selected by persons of skill in this art. For example, the rotary blades may be essentially round, with small sawtooth protuberances along the edges.

The specific arrangement of the diameters of the rotary blades and the spacers produce a specific conical outline which causes shaft 13 to be disposed at an angle Θ with respect to the surface of substrate material 11. Angle Θ is less than 90°, and also corresponds to the angle at which rotary blades 17 penetrate the substrate material.

Figure 2:
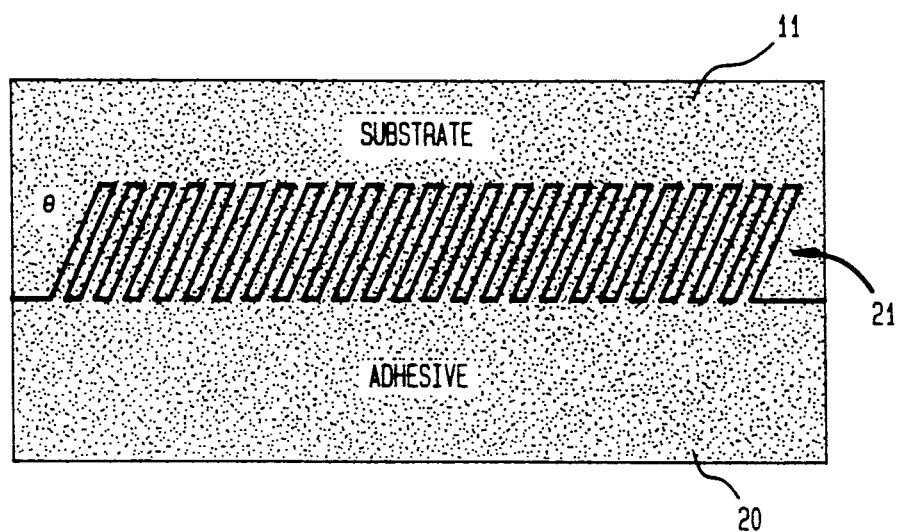
FIG. 2 is a schematic representation of the bond between the substrate material and a fluid adhesive material, after use of the rotary tool of FIG. 1.

FIG. 2 is a schematic representation of substrate material 11, after being subjected to the surface treatment of rotary tool 10, as described hereinabove. As shown, the substrate material is in engagement with an adhesive material 20. A micromechanical attachment 21 is effected by capillary flow of the adhesive material, while it is in a fluid state, into the channels cut by rotary blades 17. Upon solidification of adhesive material 20, the micromechanical attachment is made. In order to achieve the capillary flow of the adhesive material into the channels of substrate material 11, rotary blades 17 should have a thickness which produces cuts on the order of 0.5 mm.

TEST RESULTS

Tensile adhesion tests were conducted on dentin samples using three commercially available dental adhesives, marketed as SCOTCHBOND, PRISMA BOND, and ADHESIT. One set of dentin samples was roughened with silicon carbide, and another was finished using the cone shaped circular cutting burr, as described hereinabove. The adhesives were applied to the samples after the surface treatments, and stored in water after setting. Tensile testing was performed using an Instron testing machine to measure the force necessary to separate the adhesive from the dentin. The results were as follows:

TABLE 1

| Dental Adhesive | Bond Strength, kg/cm$^2$ | | % Increase |
|---|---|---|---|
| | Silicon Carbide | Cone Burr | |
| SCOTCHBOND | 72 | 112 | 56 |
| PRISMA BOND | 20 | 53 | 165 |
| ADHESIT | 23 | 61 | 172 |

The foregoing illustrates that the present invention provides a significant advantage over conventional systems, well beyond the generally accepted 5% error level of statistical tests.

Figure 3:
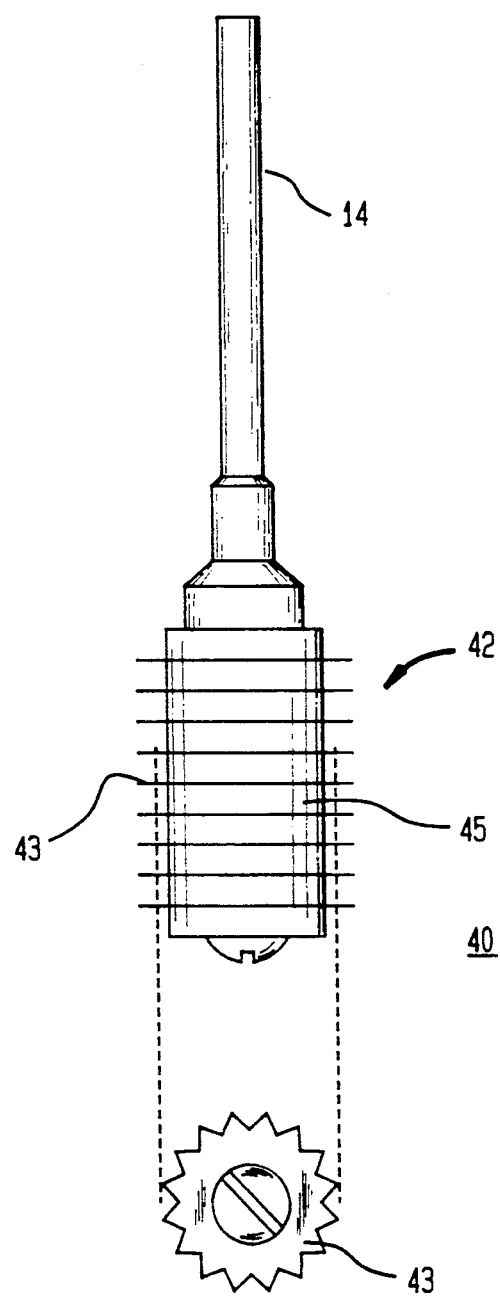
FIG. 3 is a schematic plan view of a specific illustrative embodiment having a substantially cylindrical rotary tool having an axially parallel, straight external contour.

FIG. 3 is a schematic plan view of a specific illustrative embodiment of the invention. As shown, rotary tool 40 has a shaft working end 42 having a plurality of rotary blades 43 installed thereon. In this specific embodiment, rotary blades 43 all have the same effective diameter, so as to produce a generally cylindrical external contour for the shaft working end. A plurality of spacers 45, each having the same diameter, are arranged intermediate of rotary blades 43. As shown, the generally cylindrical contour of shaft working end 42 is arranged to be coaxial with shaft coupling end 14.

Figure 4:
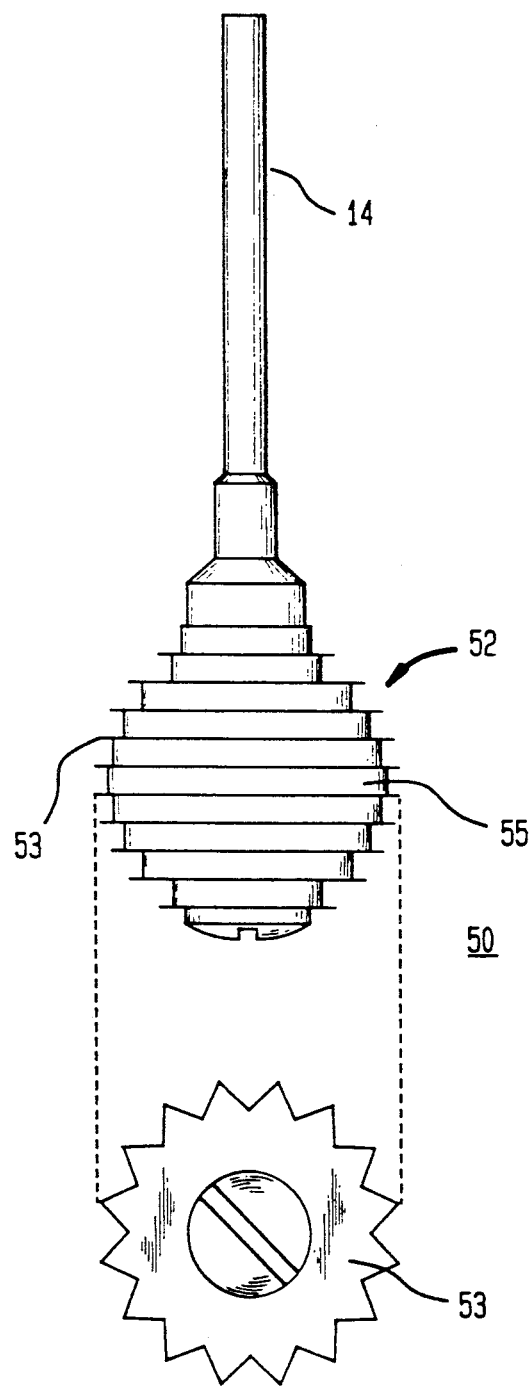
FIG. 4 is a schematic plan view of a specific illustrative embodiment of the invention having a substantially circular, or convex, external contour.

FIG. 4 is a schematic plan view of a rotary tool 50 having a shaft working end 52 wherein a plurality of rotary blades 53 of various diameters are arranged to produce a somewhat spherical outward contour. Moreover, a plurality of spacers 55, also of different diameters, are arranged intermediate of the rotary blades.

Figure 5:
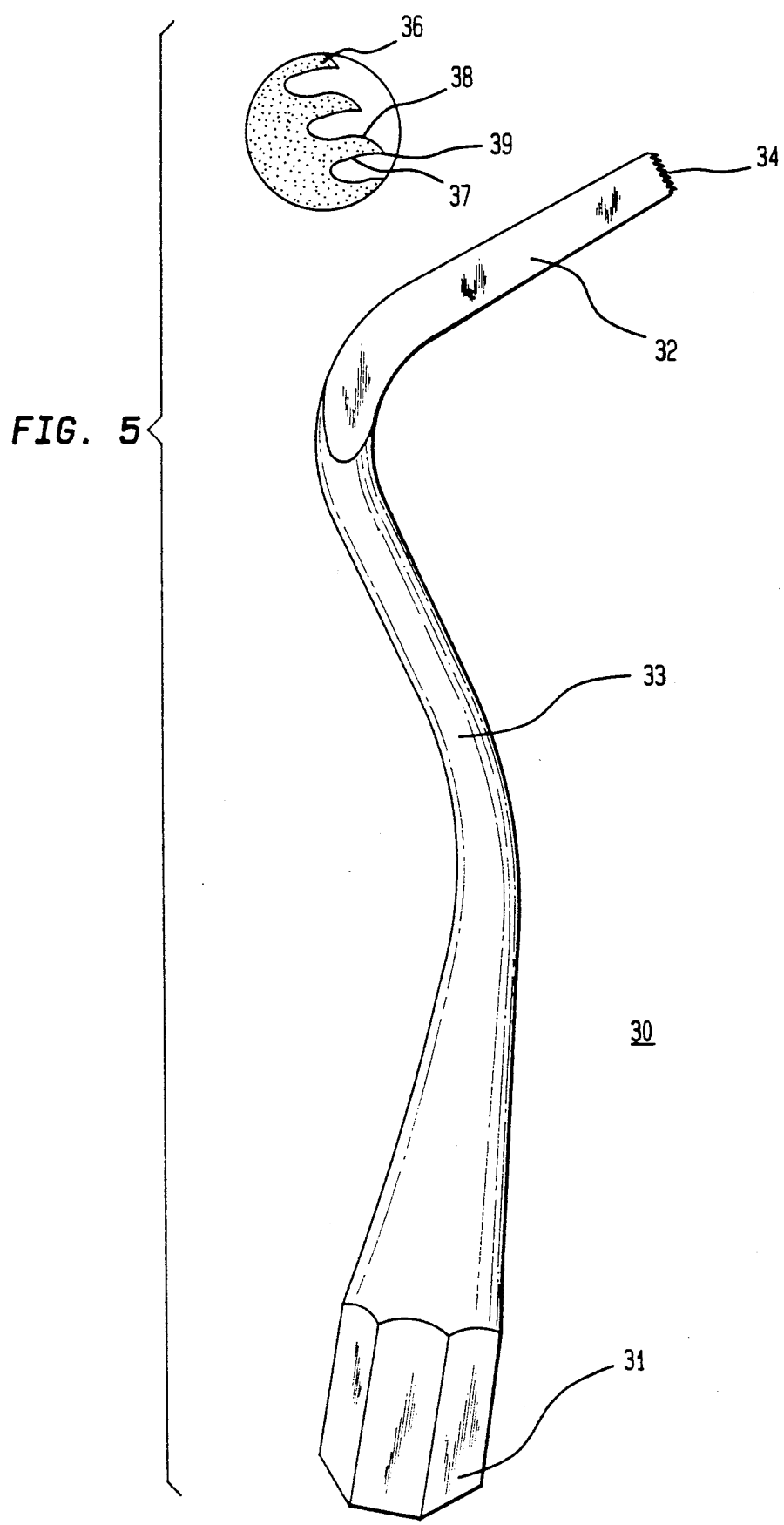
FIG. 5 is a plan view of a hand tool which is particularly adapted to the field of dentistry for producing undercuts in a tooth prior to bonding.

FIG. 5 is a plan view of a manual finisher 30 which is particularly adapted to dentistry for producing undercuts (not shown) in a tooth (not shown) prior to bonding. The manual finisher has a handle portion 31 which is coupled to a blade portion 32 by a coupling section 33. In this specific illustrative embodiment, handle portion 31, coupling section 33, and blade portion 32 are formed integrally with one another. Blade portion 32 is provided with a cutting edge 34 which, as shown in the magnified portion of the drawing, has a plurality of cutting teeth 36 formed thereon.

In the embodiment of FIG. 5, each of cutting teeth 36 has a shape with a substantially flat side 37 and a curved side 38. Substantially flat side 37 and curved side 38 meet discontinuously at a point 39 which facilitates the cutting operation. The manual finisher is operated by drawing cutting edge 34 across the surface of a tooth (not shown) so that cutting teeth 36 form respective undercuts therein.

Although the invention has been described in terms of specific embodiments and applications, persons skilled in the art can, in light of this teaching, generate additional embodiments without exceeding the scope or departing from the spirit of the claimed invention. Accordingly, it is to be understood that the drawing and description in this disclosure are proffered to facilitate comprehension of the invention, and should not be construed to limit the scope thereof.

What is claimed is:

1. A surface finishing instrument for installation on a rotating tool and for application to a surface, the surface finishing instrument comprising:
    shaft means having a coupling end for coupling to the rotating tool and rotating axially in response thereto, and a working end;
    blade means formed of a plurality of thin, substantially circular blades, each of said circular blades having a respective diameter different from the diameter of any other of said circular blades, said circular blades being mounted coaxially adjacent to one another throughout said working end of said shaft means in diametrically increasing order toward said coupling end of said shaft means, each of said circular blades cutting exclusively edgewise into the surface of a tooth of a living being for producing therein a respective elongated cut at a predetermined non-perpendicular angle with respect to the surface, said cut having a width which corresponds to a predetermined thickness of a respective one of said circular blades and being less than approximately 0.6 mm for promoting capillary flow into said cut in said tooth by an adhesive fluid; and
    a plurality of spacer means each having a predetermined thickness and being installed between said adjacent ones of said blades for maintaining a respective predetermined axial distance between said blades, whereby said adjacent cuts produced in the surface by said adjacent ones of said blades are spaced apart from one another by a distance corresponding to said respective predetermined axial distance.

2. The surface finishing instrument of claim 1 wherein said blades on said shaft means form a substantially conical outline with an outline edge at a predetermined angle $\Theta$ with respect to a longitudinal axis of said shaft means.

3. A method of finishing a surface for enhancing engagement of the surface of a tooth with a fluid dental adhesive material, the method comprising the steps of:
    forming a plurality of cuts into the surface of the tooth at a predetermined angle with respect thereto less than 90° to form respective undercuts therein, said plurality of undercuts being parallel to one another and formed simultaneously, each of said undercuts having substantially the same depth and a predetermined width between parallel walls throughout said depth which is less than approximately 0.6 mm; and
    applying the fluid dental adhesive material onto the finished surface, the fluid dental adhesive material having a viscosity characteristic which facilitates capillary flow into said undercuts.

4. The method of claim 3 wherein said step of forming comprises the further steps of:
    engaging with the surface a blade having a plurality of substantially aligned cutting teeth arranged at a predetermined angle with respect to the surface which is less than 90°; and
    drawing said blade along the surface in a direction transverse to said alignment of said cutting teeth.

* * * * *